United States Patent
Murphy et al.

(10) Patent No.: US 12,023,484 B2
(45) Date of Patent: Jul. 2, 2024

(54) SURGICAL TOOL

(71) Applicant: Cochlear Limited, Macquarie University (AU)

(72) Inventors: Richard Bruce Murphy, Auckland (NZ); Nicholas Charles Kendall Pawsey, North Ryde (AU)

(73) Assignee: Cochlear Limited, Macquarie University (AU)

( * ) Notice: Subject to any disclaimer, the term of this patent is extended or adjusted under 35 U.S.C. 154(b) by 464 days.

(21) Appl. No.: 17/405,345

(22) Filed: Aug. 18, 2021

(65) Prior Publication Data

US 2022/0032045 A1 Feb. 3, 2022

Related U.S. Application Data

(63) Continuation of application No. 15/189,420, filed on Jun. 22, 2016, now Pat. No. 11,116,963.

(51) Int. Cl.
| | |
|---|---|
| *A61N 1/05* | (2006.01) |
| *A61N 1/36* | (2006.01) |
| A61B 17/34 | (2006.01) |
| A61F 11/20 | (2022.01) |
| A61N 1/32 | (2006.01) |

(52) U.S. Cl.
CPC ....... *A61N 1/0541* (2013.01); *A61N 1/36036* (2017.08); *A61B 17/3468* (2013.01); *A61F 11/20* (2022.01); *A61N 1/327* (2013.01); *A61N 1/36038* (2017.08)

(58) Field of Classification Search
CPC ..... A61M 31/00; A61N 1/0541; A61N 1/327; A61N 1/36036; A61N 1/36038; A61B 17/3468; A61F 11/004
See application file for complete search history.

(56) References Cited

U.S. PATENT DOCUMENTS

| | | | |
|---|---|---|---|
| 6,309,410 B1 * | 10/2001 | Kuzma | A61N 1/0541 607/137 |
| 7,328,072 B2 | 2/2008 | Milojevic et al. | |
| 2012/0191032 A1 | 7/2012 | Housley | |
| 2014/0052148 A1 | 2/2014 | Vancaillie et al. | |
| 2014/0194807 A1 | 7/2014 | Housley | |

* cited by examiner

*Primary Examiner* — Jason E Flick
(74) *Attorney, Agent, or Firm* — Edell, Shapiro & Finnan, LLC

(57) ABSTRACT

Presented herein are dual-function surgical tools for insertion of implantable stimulating assemblies, such as intra-cochlear stimulating assemblies. In addition to facilitating intra-operative positioning of a stimulating assembly within a recipient (e.g., operating to guide the stimulating assembly of an implantable medical device into position), the surgical tool also includes a plurality of electrodes configured to apply an electroporation electrical field to a recipient's nerve cells to enable introduction of treatment substance into the nerve cells.

24 Claims, 15 Drawing Sheets

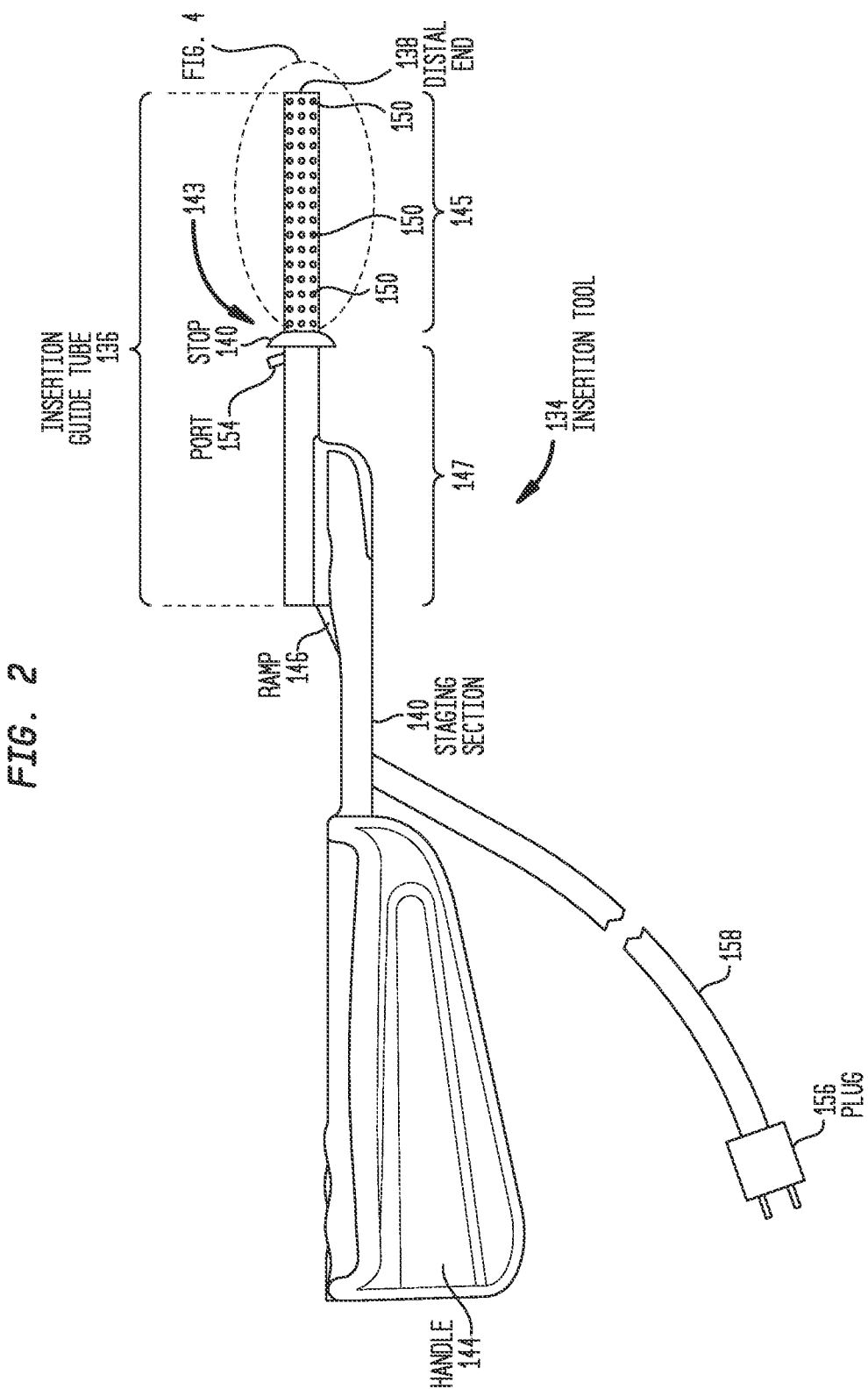

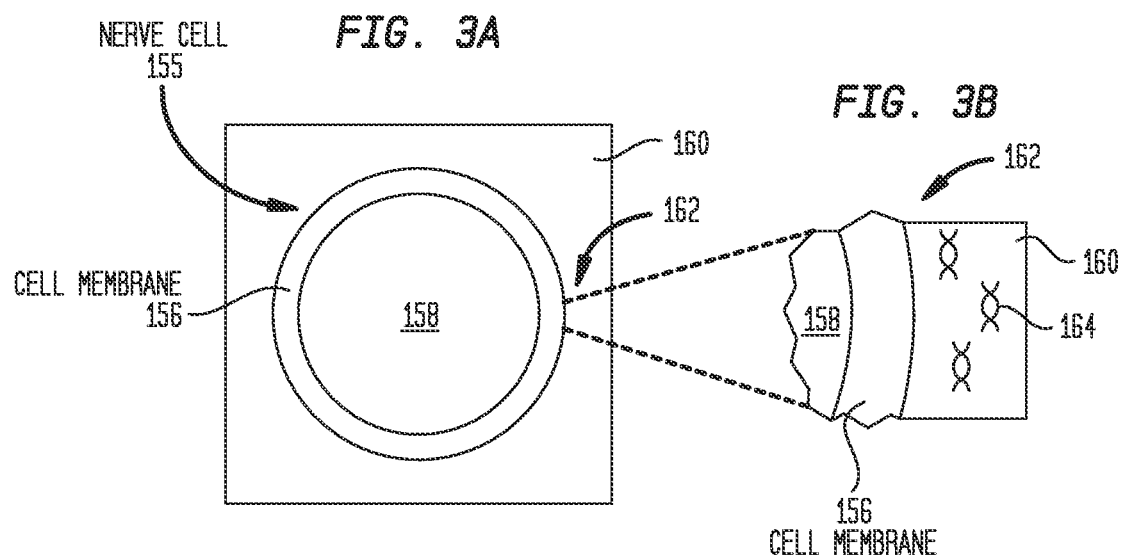
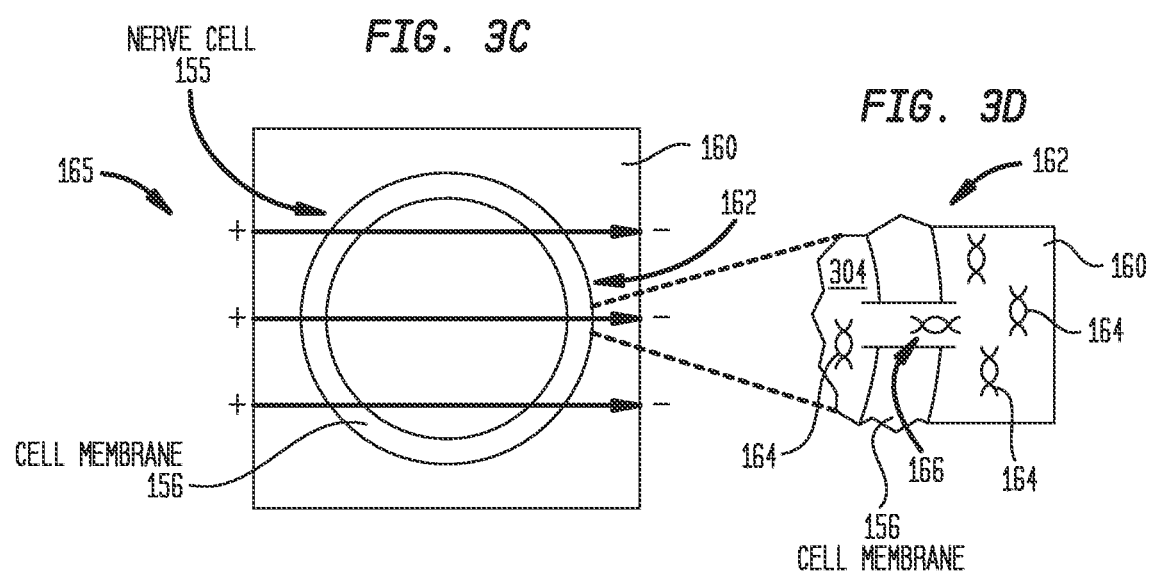

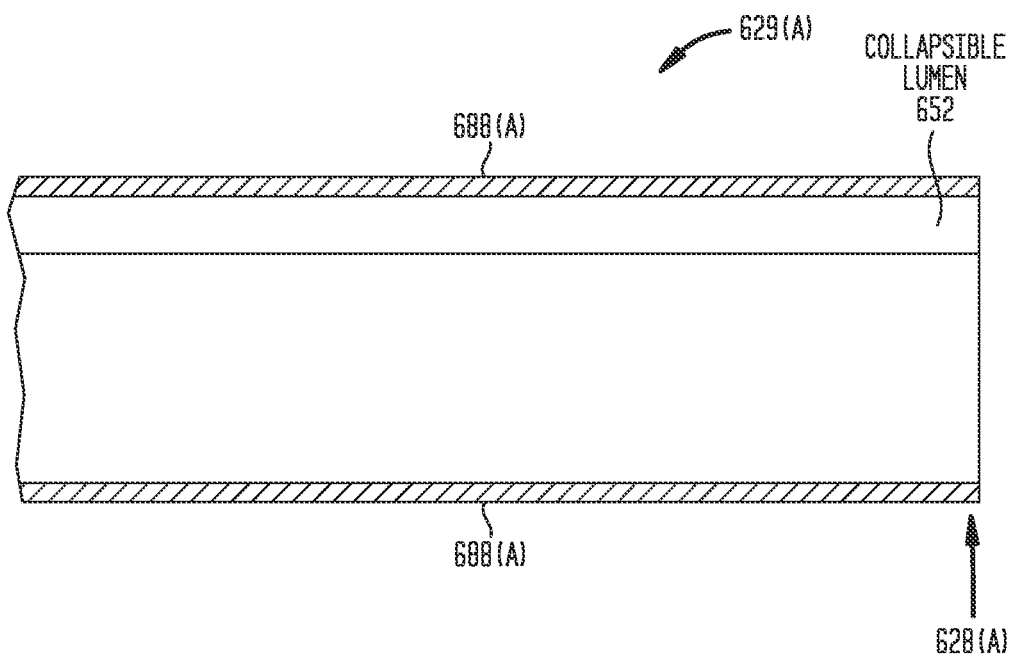
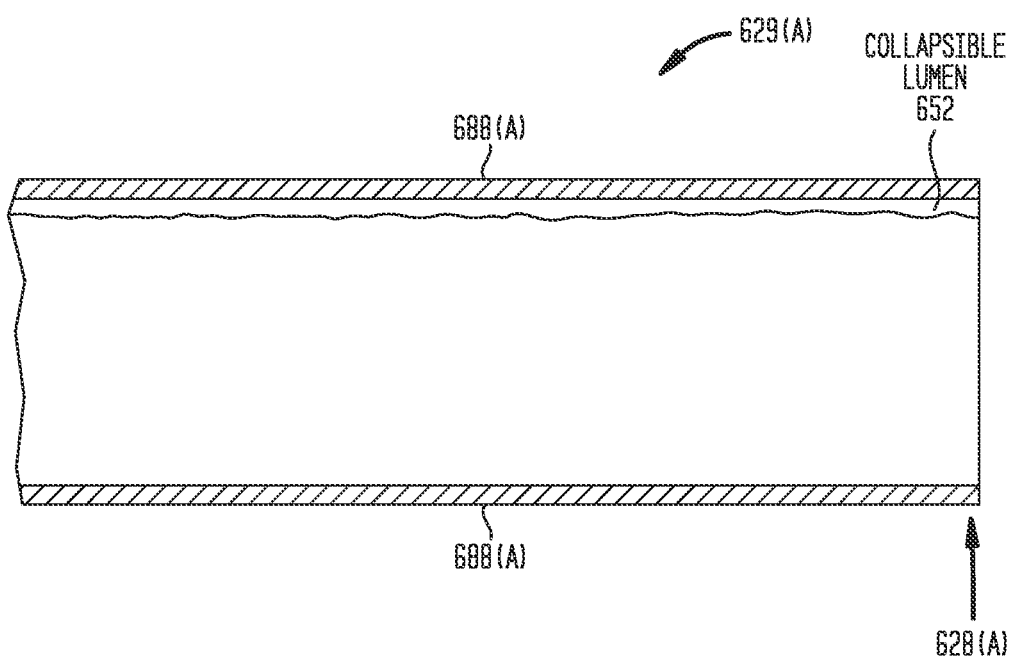

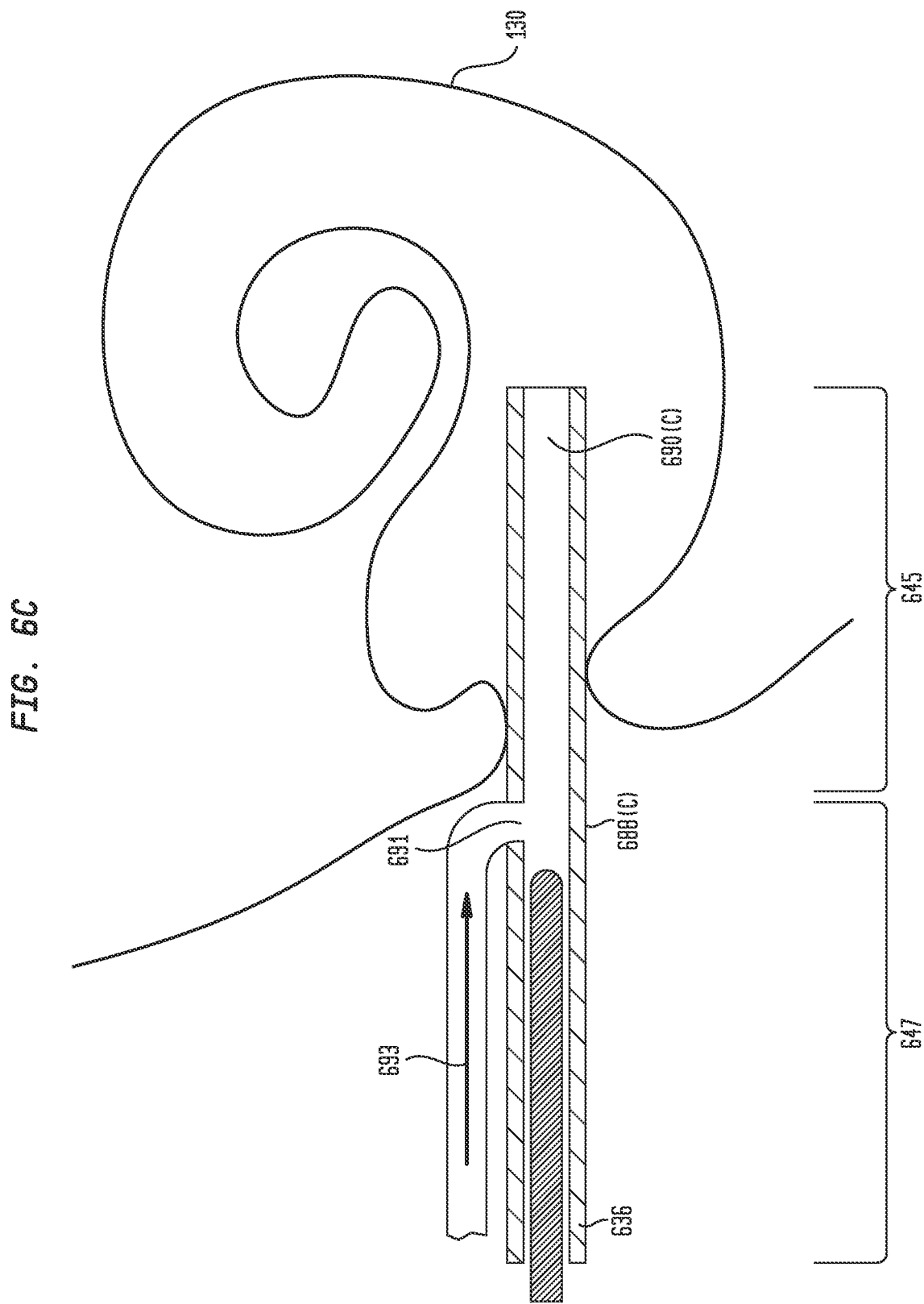

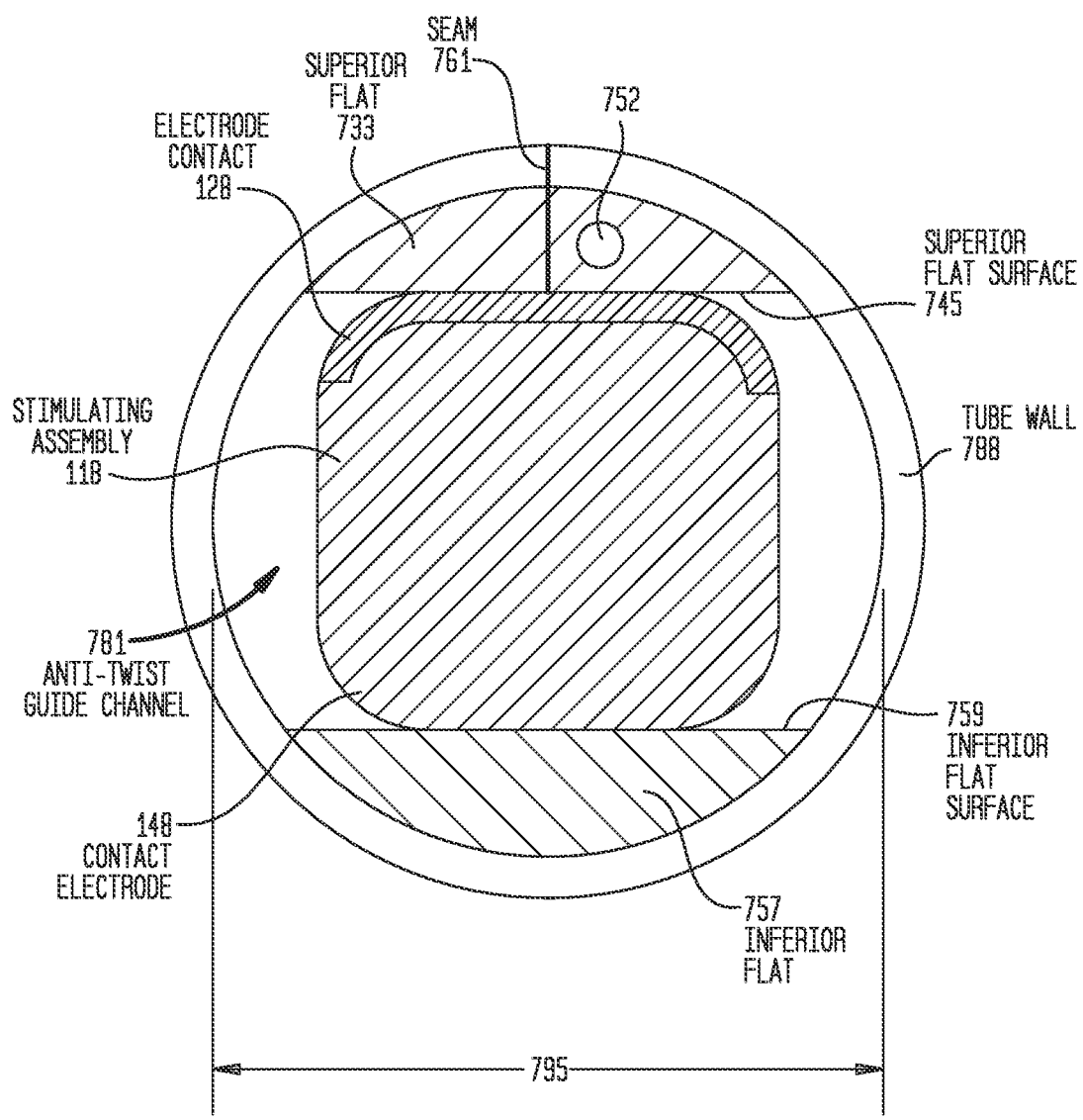

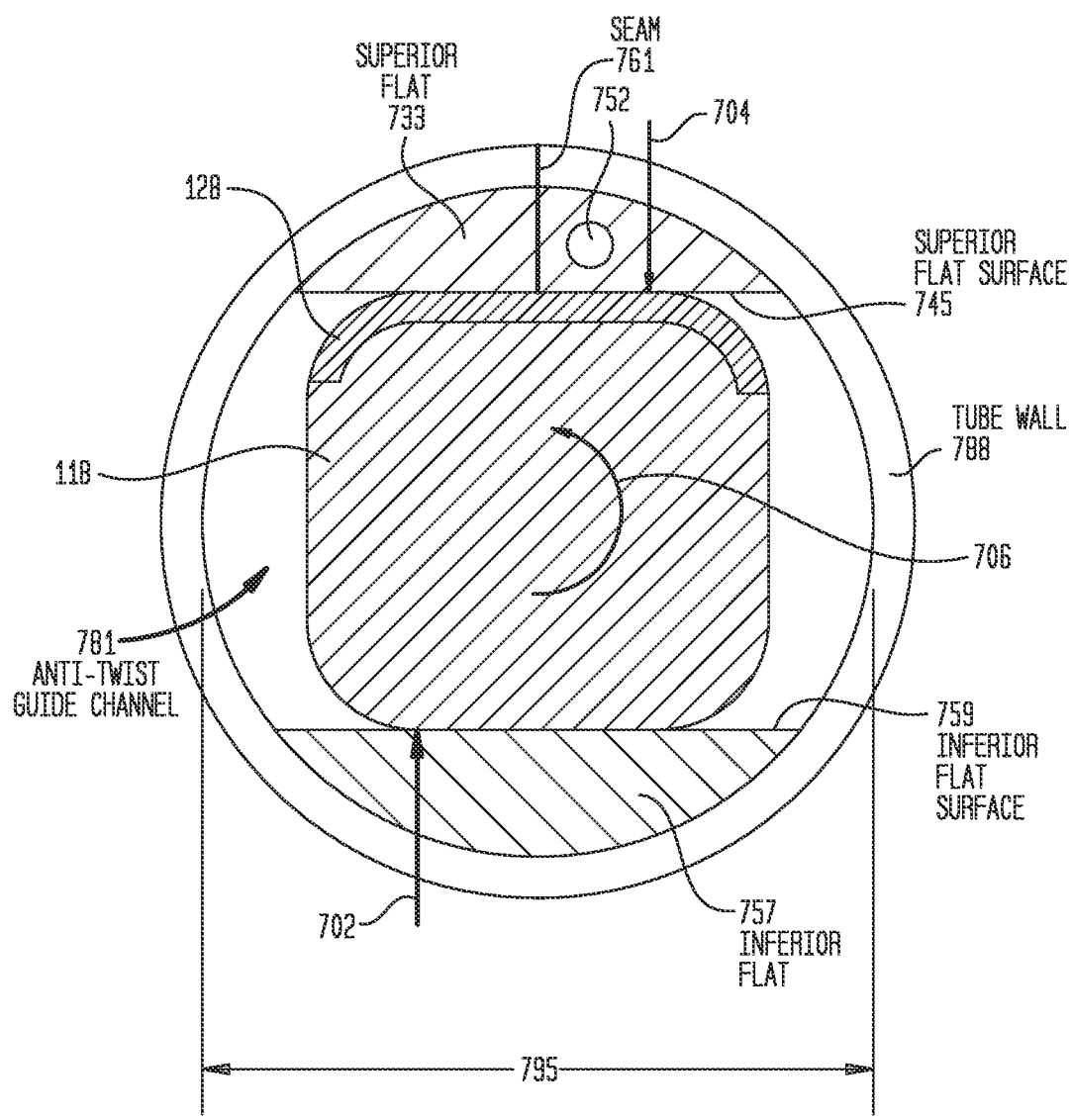

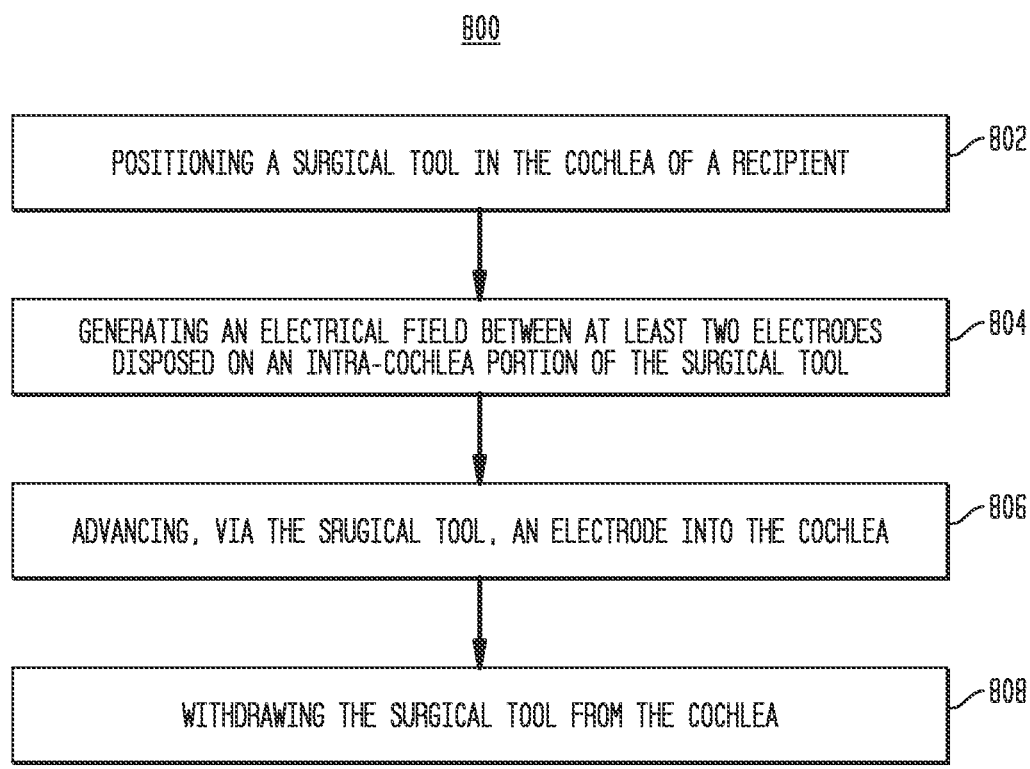

SURGICAL TOOL

BACKGROUND

Field of the Invention

The present invention relates generally to tissue-stimulating prostheses.

Related Art

There are several types of medical devices that operate by delivering electrical (current) stimulation to the nerves, muscle or other tissue fibers of a recipient. These medical devices, referred to herein as tissue-stimulating prostheses, typically deliver current stimulation to compensate for a deficiency in the recipient. For example, tissue-stimulating hearing prostheses, such as cochlear implants, are often proposed when a recipient experiences sensorineural hearing loss due to the absence or destruction of the cochlear hair cells, which transduce acoustic signals into nerve impulses. Auditory brainstem stimulators are another type of tissue-stimulating hearing prostheses that might be proposed when a recipient experiences sensorineural hearing loss due to damage to the auditory nerve.

SUMMARY

In one aspect, a surgical tool is provided. The surgical tool comprises: an intra-cochlear portion configured to be inserted into the cochlea of a recipient to guide a stimulating assembly of an implantable medical device into position within the cochlea, wherein the intra-cochlear portion of the surgical tool comprises a plurality of electrodes.

In another aspect, an insertion tool for an intra-cochlear stimulating assembly is provided. The insertion tool comprises: an insertion guide tube having an insertion lumen configured to receive the intra-cochlear stimulating assembly therein, wherein a distal portion of the insertion guide tube is configured to be positioned within a cochlea of a recipient; and one or more electrodes disposed on the distal portion of the insertion guide tube, wherein the one or more electrodes are configured to apply an electrical field to the cochlea.

In another aspect, a method is provided. The method comprises: positioning a surgical tool in the cochlea of a recipient; generating an electrical field between at least two electrodes disposed on an intra-cochlea portion of the surgical tool; advancing, via the surgical tool, an electrode into the cochlea; and withdrawing the surgical tool from the cochlea.

BRIEF DESCRIPTION OF THE DRAWINGS

Embodiments of the present invention are described herein in conjunction with the accompanying drawings, in which:

FIG. 2 is a side view of an embodiment of an insertion tool in accordance with embodiments presented herein;

FIG. 3A is a schematic diagram illustrating a nerve cell prior to introduction of a treatment substance therein via electroporation in accordance with embodiments presented herein;

FIG. 3B is a schematic diagram illustrating an enlarged view of a portion of the nerve cell of FIG. 3A;

FIG. 3C is a schematic diagram illustrating the nerve cell of FIG. 3A during introduction of a treatment substance therein via electroporation in accordance with embodiments presented herein;

FIG. 3D is a schematic diagram illustrating an enlarged view of a portion of the nerve cell of FIG. 3C;

FIGS. 6A and 6B are cross-sectional diagrams illustrating an insertion tool having a collapsible lumen for delivery of treatment substances or a recipient's cochlea in accordance with embodiments presented herein;

FIG. 6C is a cross-sectional diagram illustrating another insertion tool in accordance with embodiments presented herein;

FIG. 7D is a cross-sectional view of the stimulating assembly of FIG. 7C positioned in the insertion guide tube illustrated in FIGS. 7A and 7B;

FIG. 7E is a cross-sectional view of the stimulating assembly of FIG. 7C positioned in the insertion guide tube illustrated in FIGS. 7A and 7B with arrows representing the twisting force of the stimulating assembly and the reactive force applied to the stimulating assembly by the insertion guide tube;

FIG. 8 is a flowchart of a method in accordance with embodiments presented herein.

DETAILED DESCRIPTION

Embodiments presented herein are generally directed to dual-function surgical tools for insertion of implantable stimulating assemblies, such as intra-cochlear stimulating assemblies. In addition to facilitating intra-operative positioning of a stimulating assembly within a recipient (e.g., operating to guide the stimulating assembly of an implantable medical device into position), the surgical tool also includes a plurality of electrodes configured to apply an electroporation electrical field to a recipient's nerve cells to enable introduction of a treatment substance into the nerve cells.

As noted, there are a number of different types of tissue-stimulating prostheses that use a stimulation assembly to deliver stimulation to compensate for a deficiency in a recipient. Merely for ease of illustration, details of insertion tools in accordance with embodiments presented herein are primarily described herein with reference to the insertion of a specific type of stimulating assembly (electrode assembly), namely an intra-cochlear stimulating assembly of a cochlear implant. However, it is to be appreciated that the insertion tools presented herein may be used with other types of stimulating assemblies of other tissue-stimulating prostheses, such as spinal stimulators, vagal nerve stimulators, retinal stimulators, and deep brain stimulators.

Figure 1:
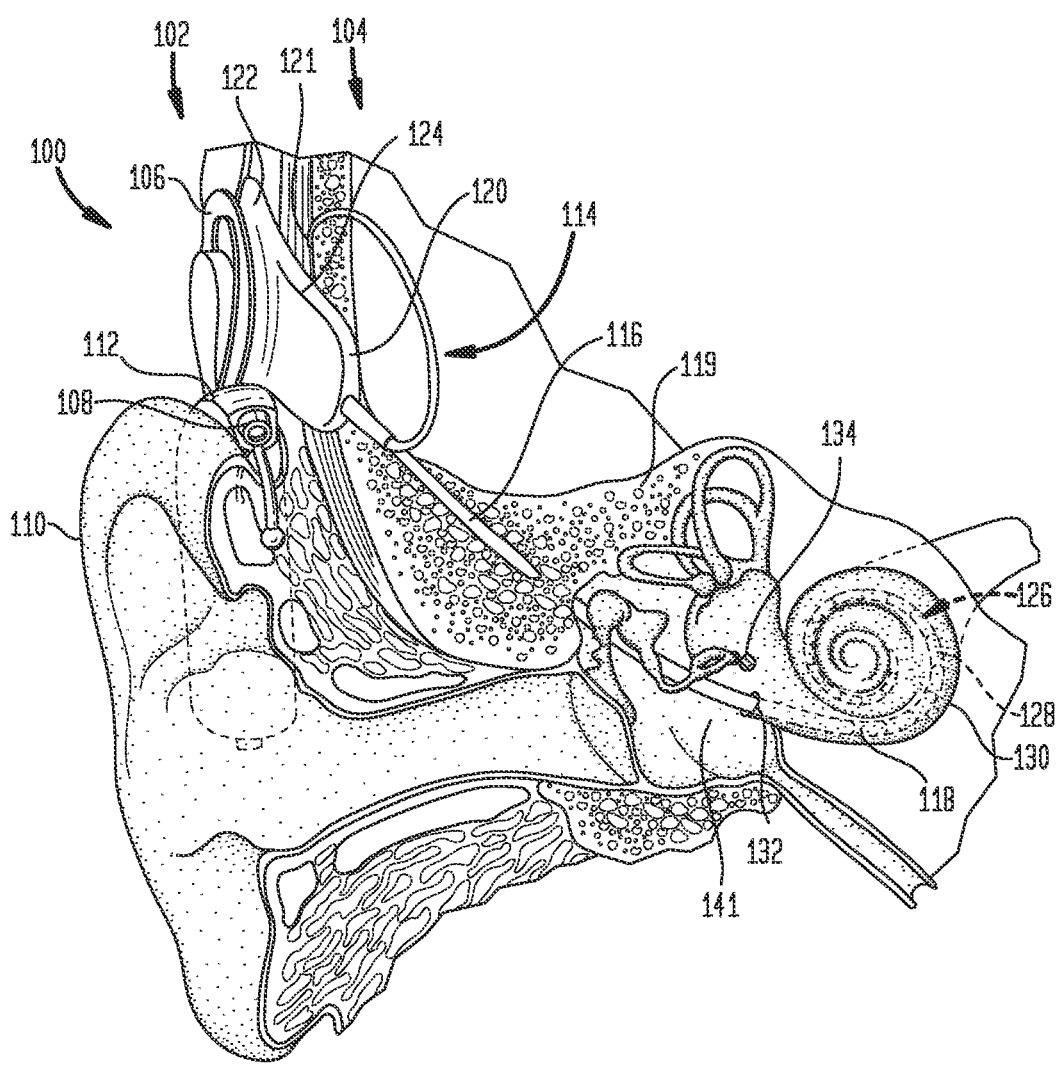
FIG. 1 is a perspective view of a cochlear implant having a stimulating assembly that may be advantageously implanted in a recipient using an embodiment of an insertion tool described herein.

More specifically, FIG. 1 is perspective view of an exemplary cochlear implant system 100 with which embodiments presented herein may be utilized. The cochlear implant system 100 includes an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more sound input elements 108 (e.g., microphones, telecoils, etc.) for detecting sound signals or input audio signals, and a sound processing unit 112. The sound processing unit 112 includes, for example, a power source (not shown in FIG. 1) and a sound processor (also not shown in FIG. 1). The sound processor is configured to process electrical signals generated by a sound input element 108 that is positioned, in the depicted embodiment, by auricle 110 of the recipient. The sound processor provides the processed signals to external coil 106 via, for example, a cable (not shown in FIG. 1).

The implantable component 104 comprises an implant body 114, a lead region 116, and an elongate intra-cochlear stimulating assembly (electrode assembly) 118. The implant body 114 comprises a stimulator unit 120, an internal/implantable coil 122, and an internal receiver/transceiver unit 124, sometimes referred to herein as transceiver unit 124. The transceiver unit 124 is connected to the implantable coil 122 and, generally, a magnet (not shown) fixed relative to the internal coil 122.

The magnets in the external component 102 and implantable component 104 facilitate the operational alignment of the external coil 106 with the implantable coil 122. The operational alignment of the coils enables the implantable coil 122 to transmit/receive power and data to/from the external coil 106. More specifically, in certain examples, external coil 106 transmits electrical signals (e.g., power and stimulation data) to implantable coil 122 via a radio frequency (RF) link. Implantable coil 122 is typically a wire antenna coil comprised of multiple turns of electrically insulated single-strand or multi-strand platinum or gold wire. The electrical insulation of implantable coil 122 is provided by a flexible molding (e.g., silicone molding). In use, transceiver unit 124 may be positioned in a recess of the temporal bone of the recipient. Various other types of energy transfer, such as infrared (IR), electromagnetic, capacitive and inductive transfer, may be used to transfer the power and/or data from an external device to a cochlear implant and, as such, FIG. 1 illustrates only one example arrangement.

Elongate stimulating assembly 118 is configured to be at least partially implanted in cochlea 130 and includes a plurality of longitudinally spaced intra-cochlear electrical stimulating contacts (electrical contacts) 128 that collectively form a contact array 126. Stimulating assembly 118 extends through an opening in the cochlea 130 (e.g., cochleostomy 132, the round window 134, etc.) and has a proximal end connected to stimulator unit 120 via lead region 116 that extends through mastoid bone 119. Lead region 116 couples the stimulating assembly 118 to implant body 114 and, more particularly, stimulator unit 120.

In general, the sound processor in sound processing unit 112 is configured to execute sound processing and coding to convert a detected sound into a coded signal corresponding to electrical signals for delivery to the recipient. The coded signal generated by the sound processor is then sent to the stimulator unit 120 via the RF link between the external coil 106 and the internal coil 122. The stimulator unit 120 includes one or more circuits that use the coded signals, received via the transceiver unit 124, so as to output stimulation (stimulation current) via one or more stimulation channels that terminate in the stimulating contacts 128. As such, the stimulation is delivered to the recipient via the stimulating contacts 128. In this way, cochlear implant system 100 stimulates the recipient's auditory nerve cells, bypassing absent or defective hair cells that normally transduce acoustic vibrations into neural activity.

Stimulating assembly 118 may be inserted into cochlea 130 with the use of an insertion tool in accordance with embodiments presented herein. FIG. 2 is a side view of an embodiment of an insertion tool 134 for implanting stimulating assembly 118 into cochlea 130. In the illustrative embodiment of FIG. 2, the insertion tool 134 includes an elongate insertion guide tube 136 configured to be partially inserted into cochlea 130. The elongate insertion guide tube 136 has a distal end 138 from which the stimulating assembly 118 is deployed into the cochlea 130. Insertion guide tube 136 also comprises a radially-extending stop 140 that may be utilized to determine or otherwise control the depth to which insertion guide tube 136 is inserted into cochlea 130. In other words, the insertion guide tube 136 includes a first section 145, referred to herein as an intra-cochlear section, that is configured to be inserted into, and subsequently withdrawn from, the recipient's cochlea 130. The intra-cochlear section 145 extends from a proximal end 143 located adjacent to the stop 140 to the distal end 138 of the insertion guide tube 136.

In the example of FIG. 2, insertion guide tube 136 also includes an extra-cochlear section 147 that is mounted on a distal region of an elongate staging section 140 on which the stimulating assembly 118 is positioned prior to implantation. A handle 144 is mounted to a proximal end of staging section 140 to facilitate implantation. The handle 144, staging section 140, and extra-cochlear section 147 collectively form an extra-cochlear portion of the insertion tool 134 that facilitates intra-operative positioning and retraction of the insertion tool 134.

During use, stimulating assembly 118 is advanced from staging section 140 into an insertion lumen (not shown in FIG. 2) of the insertion guide tube 136 via ramp 146. As described further below, after insertion guide tube 136 is inserted to the appropriate depth in cochlea 130, stimulating assembly 118 is advanced through the insertion lumen of the guide tube 136 so as to exit distal end 138.

In one embodiment, the stimulating assembly 118 is inserted into the cochlea via the round window 134 and, as such, the intra-cochlear section 145 of insertion guide tube 136 is sized to fit through the opening covered by the round window membrane. For example, the outer diameter (or diameter equivalent) of the intra-cochlear section 145 can be about 1 mm, 1.1 mm, 1.2 mm, 1.3 mm, 1.4 mm, 1.5 mm, or 1.6 mm. The size of the lumen within the insertion guide tube generally matches the stimulating assembly (although the insertion guide tube can accommodate oversized stimulating assemblies by, for example, splaying along a seam as the electrode is advanced). The stimulating assembly 118 can have a diameter of between about 0.3 mm and about 1.2 mm. Contemporary stimulating assemblies have a diameter that is approximately 0.8 mm at its thickest point, but the distal end (tip) of the stimulating assembly can have a significantly smaller diameter, such as approximately 0.3-0.5 mm.

In addition to enabling insertion of the stimulating assembly 118 into the cochlea 130, the insertion tool 134 of FIG. 2 is also configured to introduce substances into the recipient's cochlear nerve cells via electroporation. In other words, as described further below, the insertion tool 134 is a dual-function device that is configured to deliver an electrical field to open pores in the cochlear nerve cells to enable the introduction of substances thereto, as well as to enable intra-operative placement of the stimulating assembly 118 into the cochlea 130. The substances that the insertion tool 134 introduce into the cochlear nerve cells are generally and collectively referred to herein as "treatment substances" and may include, but are not limited to, biological or bioactive substances, chemicals, pharmaceutical agents, nanoparticles, ions, Deoxyribonucleic acid (DNA) molecules, Ribonucleic acid (RNA) molecules, proteins such as Brain-derived neurotrophic factors, peptides, RNAi, viral vectors etc.

To enable the introduction of treatment substances via electroporation, the insertion tool 134 includes a plurality of electrodes 150. Also included in the insertion tool 134 is an electrical connection between the electrodes 150 and a current source (e.g., external power source) so that electroporation stimulation is provided to the electrodes. For ease of illustration, only a portion of the electrical connection between the electrodes 150 and the current source, namely a plug 156 and an electrical cable 158, are shown in FIG. 2. However, further details of example electrical connections are provided below.

Although FIG. 2 illustrates the use of a plug 156 in the electrical connection between the electrodes 150 and the external power source, it is to be appreciated that other types of electrical connectors and other electrical connections may be used in other embodiments presented herein. For example, in other embodiments the insertion tool 134 can incorporate a battery, the electrodes 150 can be electrically connected to cochlear implant 100, etc.

The insertion tool 134 can also include a substance delivery mechanism formed, in the specific example of FIG. 2, by a substance delivery lumen (not shown in FIG. 2) and a syringe port 154. That is, a treatment substance is delivered into the recipient's cochlea 130 via the syringe port 154 and a lumen extending through the intra-cochlear portion 147 of the insertion guide tune 136. In one example, at least the distal end 138 of the insertion guide tube 136 is first inserted into the cochlea 130 via an opening (e.g., the round window, oval window, cochleostomy, etc.) through which the stimulating assembly 118 is to be inserted into the cochlea. With a syringe (not shown in FIG. 2) fluidically coupled to the syringe port 154, a treatment substance is forced from the syringe through the substance delivery lumen and out the distal end into the cochlea 130. As described further below, embodiments presented herein may make use of a number of other substance delivery mechanisms.

Once the treatment substance is delivered into the cochlea 130, the electrodes 150 are configured to generate an electric field within the cochlea that increases the permeability of neural cell membranes. In other words, current signals (electroporation stimulation) are delivered to electrodes 150 in a manner that results in the generation of an electrical field, sometimes referred to herein as an electroporation electric field, that causes electroporation of the membranes of cochlear neural cells (i.e., creates pores or openings in the cell membranes). As a result, the treatment substance can pass into the nerve cells through electrically opened pores in a cell membrane. As used herein, "electroporation" refers to the application of an electrical field to a cell such that pores are opened in the cell membrane.

Before describing further details of insertion tools in accordance with embodiments presented herein, a brief explanation of electroporation and introduction of a treatment substance into a cell is first provided below with reference to FIGS. 3A-3D. More specifically, FIGS. 3A and 3C are schematic diagrams illustrating a nerve cell prior to and during, respectively, electroporation in accordance with embodiments presented herein. FIGS. 3B and 3D are enlarged views of a portion of the nerve cell shown in FIGS. 3A and 3C, respectively.

FIG. 3A is a schematic diagram of a natural nerve cell 155 at rest prior to delivery of an electroporation electric field. As shown, the nerve cell 155 comprises a cell membrane 156 that separates the interior 158 of the nerve cell 155 from the surrounding area 160. Generally, the area 160 is a fluid filled space.

FIG. 3B is an enlarged view of a portion 162 of nerve cell 155, including a portion of the cell interior 158, a portion of the cell membrane 156, and the area 160 adjacent to the portion 162 of the cell membrane. As shown in FIG. 3B, elements 164 of a treatment substance are disposed in the area 160 adjacent the nerve cell 155.

As shown in the schematic diagram of FIG. 3C, once the treatment substance (i.e., elements 164) is introduced into the proximity of the nerve cell 155, an electrical potential (i.e., voltage difference) 165 is applied across the nerve cell 155 by electrodes of an insertion tool in a manner that causes electroporation of the nerve cell. More specifically, as shown in FIG. 3D, the electrodes of an insertion tool, such as electrodes 150 of insertion tool 134, generate an electrical field that creates an electrical potential across the nerve cell 155 that, in turn, opens up pores 166 in the cell membrane 156. The electrically opened pores 166 allow the elements 164 of the treatment substance to enter the nerve cell 155 through the cell membrane 156 (i.e., as the potential difference is applied to the cell, the electrically opened pores in the cell membrane allow material to flow into the cell). After the electrical potential 165 is removed, the pores 166 in the cell membrane 156 close such that the elements 164 of the treatment substance remain in the nerve cell 156.

Figure 4A:
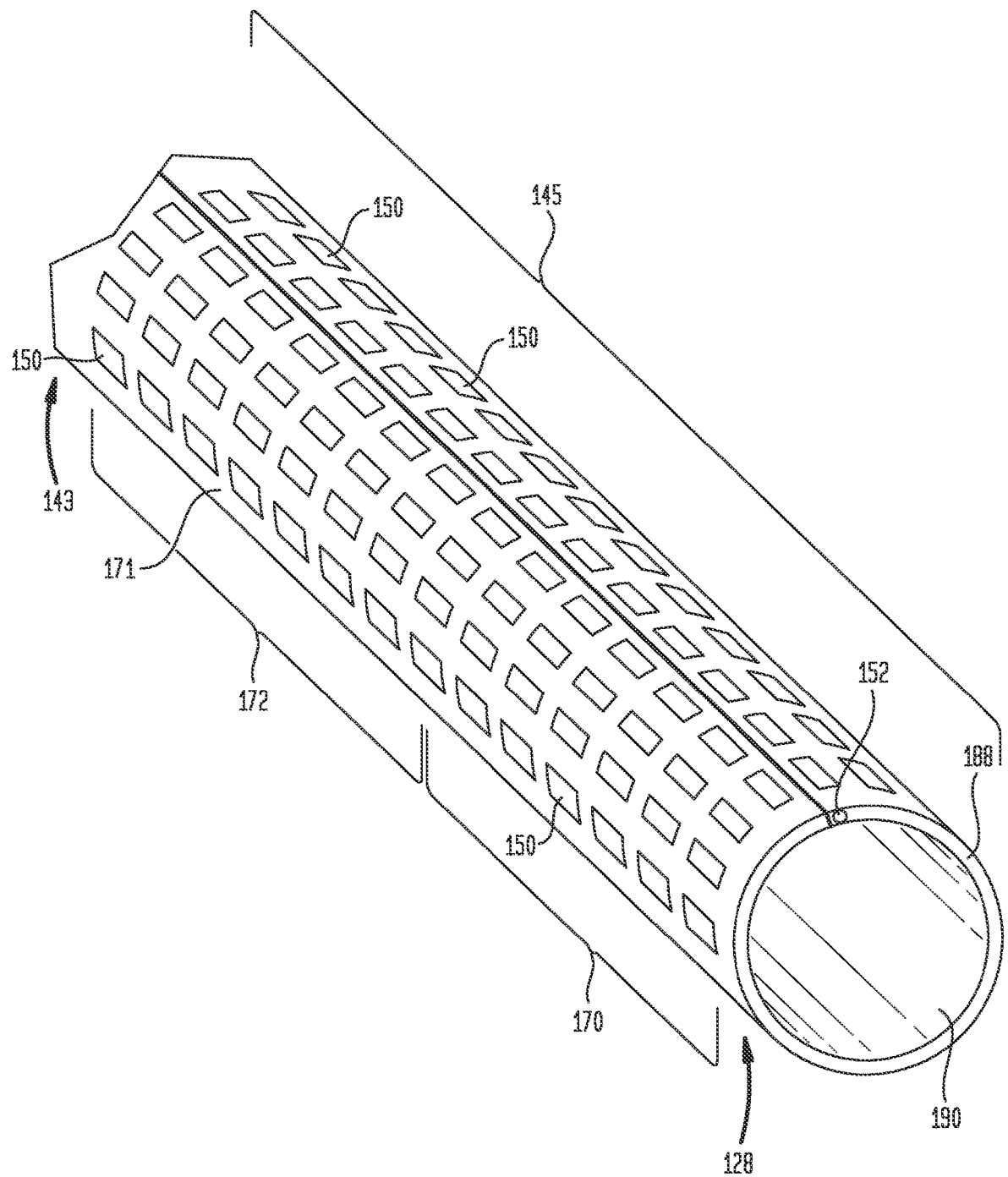
FIG. 4A is a perspective view of an intra-cochlear portion of an insertion tool in accordance with certain embodiments presented herein.

FIG. 4A is a perspective view of the intra-cochlear section 145 of insertion guide tube 136 of FIG. 2. As shown in FIG. 4A, a plurality of electrodes (electrical stimulating contacts) 150 are located at the outer surface 171 of the intra-cochlear section 145, namely on the outer surface of an outer wall 188. The electrodes 150 may be disposed on one or more selected portions of the outer surface 171 or may circumferentially surround the longitudinal length of the outer surface 171.

The electrodes 150 are electrically connected to a power supply (current source) via an electrical connector and one or more leads, such as wires or traces, (not shown in FIG. 4A) extending through or along the intra-cochlear section 145. Some embodiments of the insertion tool 134 include an electrical cable 158 and electrical connector (e.g., plug 156) to connect the electrode leads to an external current source. Alternatively, the insertion tool 134 can incorporate a battery, such as a rechargeable Li-Ion battery pack or replaceable batteries that are housed in a sealed compartment (allowing the tool to be adequately sterilized). In both embodiments, the electrodes 150 are electrically isolated from any power source of the cochlear implant 100.

As noted, the electrodes 150 are configured to generate an electric field within the cochlea 130 that causes electroporation of the cochlear nerve cells. In one arrangement, the electrical field is generated via the delivery of charge-balanced biphasic waveforms (i.e., electroporation stimulation) to two groups of electrodes 150, wherein the two groups alternatively source and sink the current. More specifically, a charge-balanced biphasic waveform comprises first and second current pulses having equal amplitude and duration, but an opposite polarity (i.e., one positive pulse and one negative pulse). Since the positive pulse equals the negative pulse, ideally, the net charge transferred to the cochlea cells is zero. In certain embodiments, the current pulses have an amplitude in the range of 40-60 milliamps.

In one example, a first current pulse having a first polarity is delivered in a first direction between two or more of the electrodes 150, and then a second pulse having the reverse polarity is delivered in a second direction between the two or more electrodes 150. In operation, such a biphasic waveform is driven between the two or more electrodes 150 a number of times (e.g., five times) in a selected pattern to affect the electroporation.

In one specific arrangement, the electrodes 150 are separated into two functional groups based on their relative position within the intra-cochlear section 145, and these two electrode groups receive the biphasic waveforms. More specifically, FIG. 4A illustrates that the electrodes 150 located relatively closer to the distal end 128 of the insertion guide tube 136 (e.g., the distal half of the electrodes) form a distal electrode group 170. The electrodes 150 within the distal electrode group 170 are electrically connected to the power supply in manner that allows all of the electrodes in the group to receive substantially the same current signals from the power supply. In other words, the electrodes 150 within the distal electrode group 170 functionally operate as a single large electrode so as to collectively deliver biphasic current pulses (i.e., half of a biphasic waveform) to the cochlea 130 with a first polarity.

FIG. 4A also illustrates that the electrodes 150 located relatively closer to the proximal end 143 of the insertion guide tube 136 (e.g., the proximal half of the electrodes) form a proximal electrode group 172. The electrodes 150 within the proximal electrode group 172 are electrically connected to the power supply in manner that allows all of the electrodes to receive substantially the same current signals from the power supply. In other words, the electrodes 150 within the proximal electrode group 172 functionally operate as a single large electrode so as to collectively deliver a biphasic current pulse (i.e., half of a biphasic waveform) to the cochlea 130 with a second (opposite) polarity.

During delivery of a biphasic current pulse via the distal electrode group 170, the electrodes 150 in the proximal electrode group 172 operate as returns for the delivered current. That is, the delivered current passes from the electrodes 150 of distal electrode group 170 to the electrodes 150 of the proximal electrode group 172. Similarly, during delivery of a biphasic current pulse via the proximal electrode group 172, the electrodes 150 in the distal electrode group 170 operate as returns for the delivered current. That is, the delivered current passes from the electrodes 150 of proximal electrode group 172 to the electrodes 150 of the distal electrode group 170.

In one example, the biphasic waveforms are provided in a square wave configuration where the pulses each have duration in the range of approximately 100 μs to approximately 500 ms. For example, the biphasic waveforms can have a duration (pulse width) of approximately 5 ms, 10 ms, 15 ms, 20 ms, 25 ms, 30 ms, 35 ms, 40 ms, 45 ms, or 50 ms. Multiple pulses are commonly used. The number of electroporation pulses administered is typically in the range of 5 to 200 pulses in total. The interval between each pulse can be about 1, 2, 3, 4, 5, 6, 7, 8, 9, or 10 seconds. Ramped waveforms can be used in at least some embodiments, as ramped waveforms can provide a faster onset of electroporation dielectric breakdown of the cell membrane, while minimizing current delivery.

FIG. 4A illustrates a specific example in which the electrodes 150 are formed into two functionally separate electrode groups that deliver a form of bipolar stimulation. That is, in these arrangements, the electroporation electrical field is generated via the delivery of charge-balanced biphasic current to two groups of electrodes 150, wherein the two groups alternatively source and sink the current. However, it is to be appreciated that the electrodes of an insertion tool in accordance with embodiments presented herein may be formed in a number of different arrangements for delivery of pulses.

It is also to be appreciated that insertion tools in accordance with embodiments presented herein can make use of a number of different electrical stimulation strategies or modes including, for example, using monopolar stimulation, multipolar stimulation, common ground mode, etc. to cause electroporation of the cochlea nerve cells. In general, the various stimulation modes that may be used in the embodiments presented herein differ from another in the shape of the electrical field generated within each stimulation mode. In these different modes, the electrodes 150 may be organized into different functional groups an/or configurations. For example, in one embodiment, the electrodes 150 are arranged so as to generate a wide electrical field that causes electroporation of a substantially large population of nerve cells. The wide electrical field may be generated, for example, using a bipolar stimulation mode, a common ground stimulation mode, a monopolar stimulation mode, etc.

In certain embodiments, it may be desirable to limit the area of nerve cells that are subject to electroporation. For example, it may be useful to cause electroporation of nerve cells in a small part of the cochlea having non-functional hair cells without affecting other parts of the cochlea. To this end, embodiments may make use of a stimulation mode where a subset of the electrodes 150 operates in accordance with a stimulation mode that generates a narrow or focused electrical field. The focused electrical field may be generated, for example, using multipolar stimulation (sometimes referred to as phased array stimulation).

In accordance with certain embodiments, multipolar or other focused stimulation modes may be used to "steer" the electric field to other regions of the cochlea and/or the surrounding area so that electroporation can occur at other sites. Since some types of cells can be damaged by repetitive stimulation, multipolar or other focused stimulation modes could be used to steer the electroporation electric field away from these types of cells.

As noted, FIG. 4A illustrates an embodiment in which the electrodes 150 are located on the intra-cochlear region 145 of the insertion guide tube 136. Depending on the insertion technique and location of the cochlear opening through which the insertion guide tube 136 is introduced into the cochlea 130, the intra-cochlear region 145 may need to bend/flex. As such, the intra-cochlear region 145 of the insertion guide tube 136 is formed from an at least partially flexible material. The use of a plurality of relatively small electrodes, as shown in the arrangement of FIG. 4A, rather than a few larger electrodes allows the intra-cochlear region 145 to retain the ability to bend/flex.

In certain embodiments, the electrodes 150, as well as the leads connecting the electrodes to a power supply, may be formed as part of a thin-film circuit that forms at least part of the outer wall 188. More specifically, in these embodiments, the outer wall 188 of the insertion guide tube 136 is configured as a substrate on which the electrodes 150 and traces (i.e., the leads) are formed via thin-film deposition (i.e., electrodes and traces are printed, etched or otherwise formed as a metal layer on the polymer substrate forming the outer wall of the insertion guide tube). Parts of the thin-film circuit can be coated with a biocompatible elastomer (such as medical grade silicone) to tune the mechanical properties of the intra-cochlea section of insertion guide tube 188. Electrodes 150 are generally disposed on or recessed in the outer surface 171 of the outer wall 188.

The thin-film circuit can be formed into a sheath that comprises the intra-cochlea portion of the insertion tool. The outer dimensions of the sheath are generally defined by the size of the opening used to insert the stimulating assembly into the cochlea (such as the round window) and the prescribed insertion depth for the intra-cochlea section of the tool 100. The size of the lumen or passage through the sheath is generally defined by the stimulating assembly the insertion tool 100 is paired with. The sheath can have an outer diameter of between about 1 mm and about 2 mm. The sheath can be configured to partially collapses or compresses to fit an opening in the cochlea where the outer diameter is marginally larger than the opening. The inner diameter of the sheath (the diameter of the lumen) is generally between about 0.4 mm and 1 mm. For example, the outer diameter can be about 1.2 mm, 1.3 mm, 1.4 mm or 1.5 mm, and the diameter of the lumen can be about 0.5 mm, 0.6 mm, 0.7 mm or 0.8 mm. The thin-film circuit can extend into the extra-cochlea portion of the tool to facilitate mechanical and electrical connection between the respective (intra-cochlea and extra-cochlea) portions of the tool 100. The extra-cochlea portion of the tool can include sections of the thin-film circuit can also extend into an extra-cochlea section of the tool.

Thin-film deposition is an example of a technique that may be used to form the electrodes and leads of an insertion tool. In other embodiments, the electrodes 150 may comprise metallic (e.g., platinum) contacts and the leads may comprise wires welded to the contacts. In these embodiments, the wires pass through the insertion guide tube 136 for connection of the electrodes 150 to the power supply.

Figure 4B:
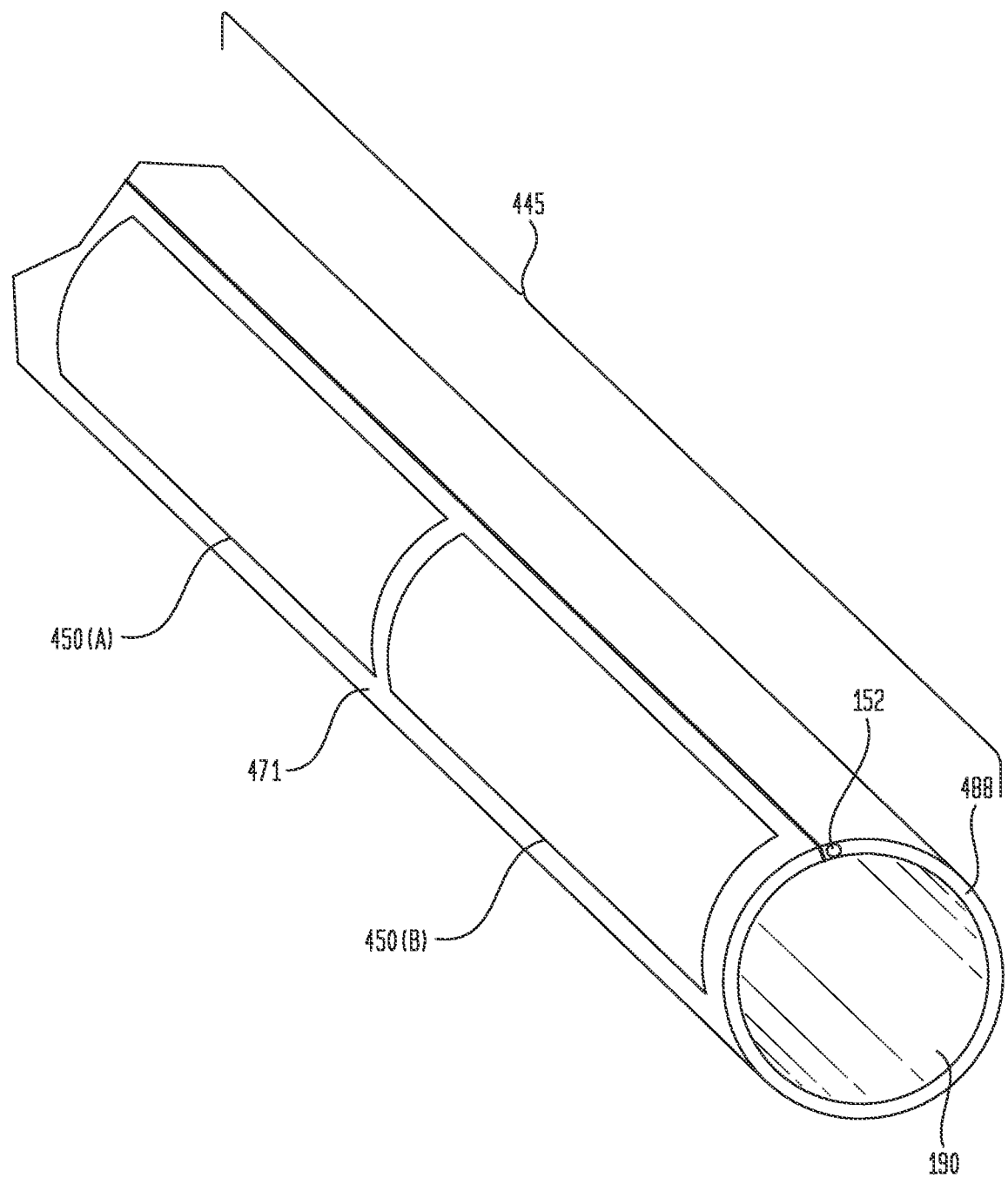
FIG. 4B is a perspective view of an intra-cochlear portion of an insertion tool in accordance with alternative embodiments presented herein.

FIG. 4A illustrates an arrangement in which an insertion tool includes a relatively large number of small electrodes to deliver electroporation stimulation to a recipient. FIG. 4B is a perspective view of an intra-cochlear section 445 of another insertion guide tube in accordance with embodiments presented herein that makes use of two relative large electrodes 450(A) and 450(B) to deliver electroporation stimulation. More specifically, electrodes 450(A) and 450(B) are located at the outer surface 471 of the intra-cochlear section 445, namely on the outer surface of an outer wall 488. The electrodes 450(A) and 450(B) can be disposed on one or more selected portions of the outer surface 471 or can circumferentially surround portions of the outer surface 471. In on example, the electrodes 450(A) and 450(B) can half-band platinum electrodes.

The electrodes 450(A) and 450(B) are electrically connected to a power supply (current source) via one or more leads, such as wires or traces, (not shown in FIG. 4B) extending through or along the intra-cochlear section 445. The electrodes 450(A) and 450(B) are configured to generate an electric field within a recipient's cochlea that causes electroporation of the cochlear nerve cells. In one arrangement, the electrical field is generated via the delivery of charge-balanced biphasic waveforms to the electrodes 450 (A) and 450(B), wherein the two electrodes alternatively source and sink the current. That is, first current pulse having a first polarity is delivered in a first direction between two electrodes 450(A) and 450(B, and then a second pulse having the reverse polarity is delivered in a second direction between the two electrodes 450(A) and 450(B). In operation, such a biphasic waveform is driven between the two or more electrodes 450(A) and 450(B) a number of times (e.g., five times) in a selected pattern to cause electroporation of the cochlea cells.

In certain embodiments, the electrodes of an insertion tool are functionally organized in a pre-selected arrangement (e.g., preset hardwired arrangement) that delivers electrical stimulation in accordance with a pre-selected stimulation mode. However, in other embodiments, the functional arrangement of the electrodes and/or the utilized stimulating mode is configurable (adjustable). For example, FIG. 5 is a schematic diagram illustrating an electroporation control module 175 that may be disposed in the electrical connection 173 between electrodes of an insertion tool, such as electrodes 150 of insertion tool 134, and a current source 176, such as an auxiliary (e.g., external) power supply.

As shown, the electroporation control module 175 comprises a switching circuit 178 and a controller 180. The switching circuit 178 comprises a plurality of switches (not shown in FIG. 5) that are selectably connectable to either a positive signal line 182 of the current source 176 (e.g., a wire connected to the positive pin of the external power supply) or a negative signal line 184 of the current source 176 (e.g., wire connected to the negative pin of the external power supply). The switches in the switching circuit 178 are also selectably connectable to the electrodes that, in the arrangement of FIG. 5, are labeled as electrodes 150(1)-150(N), via leads 185 (e.g., wires or traces). In general, the switching circuit 178 may have a number of different configurations/arrangements that enable the electrodes 150(1)-150(N) to functionally operate as different groups that generate electroporation electrical fields in accordance with various different stimulation modes.

Figure 5:
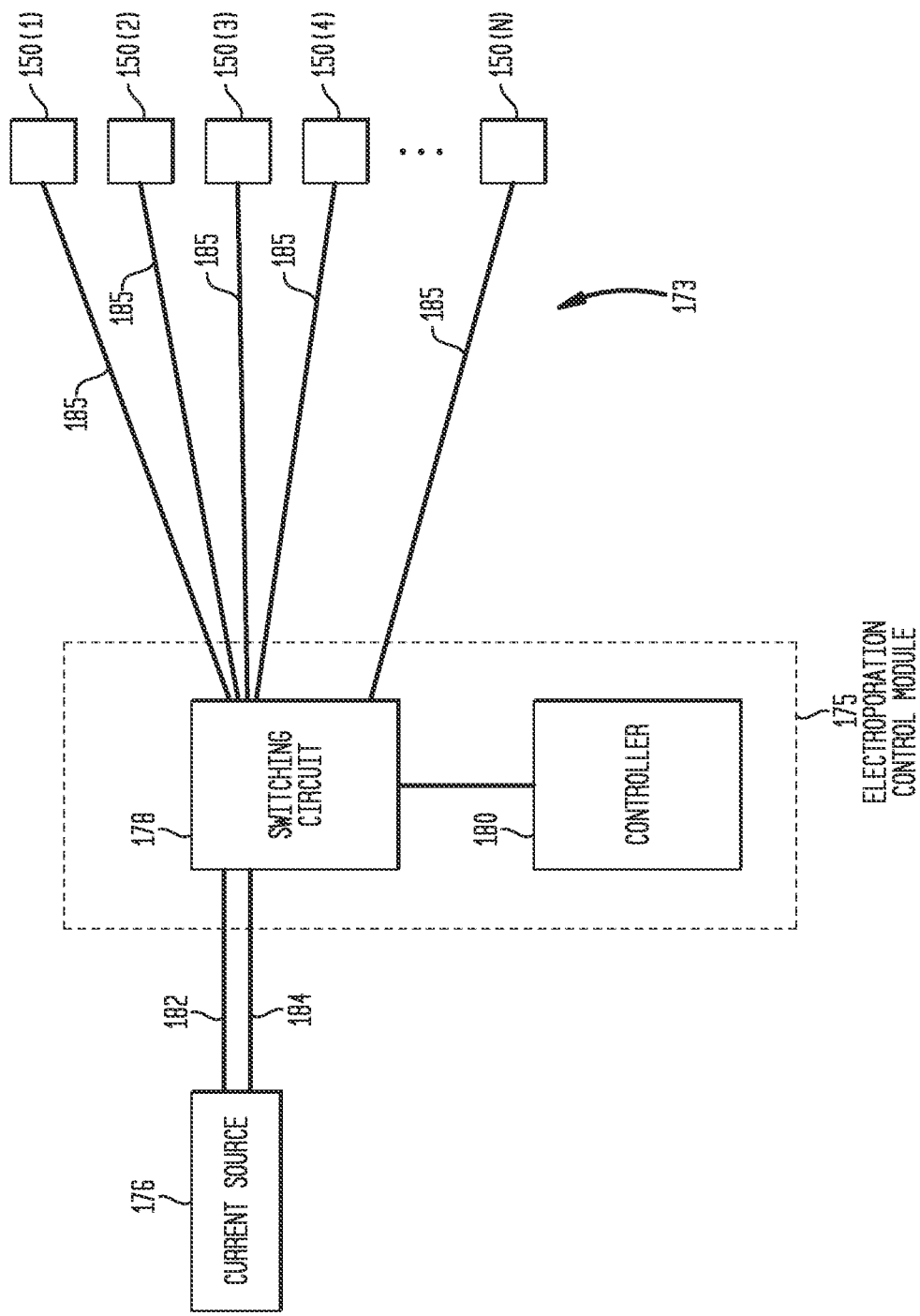
FIG. 5 is a schematic diagram illustrating an electroporation control module in accordance with embodiments presented herein.

In addition, although FIG. 5 illustrates that the electrodes 150(1)-150(N) are each connected to the switching circuit 178 via separate leads 185, it is to be appreciated that a plurality of the electrodes may be electrically connected to the switching circuit 178 via the same lead. In other words, subsets of the electrodes 150(1)-150(N) may be hardwired as preset groups where each preset group of electrodes is connected to the switching circuit 178 via a single lead. In such embodiments, all the electrodes in the preset group of electrodes are activated together/simultaneously and functionally operate as a substantially larger contact.

As noted, the electroporation control module 175 also comprises a controller 180. The controller 180 comprises, for example, a microprocessor or digital logic gates in one or more application-specific integrated circuits (ASICs), and operates to control the arrangement of the switching circuit 178 and, in turn, the arrangement of the electrodes 150(1)-

150(N) and the stimulation mode of the current signals. In certain embodiments, the controller 180 may include, or be connected to, a user interface that allows a user to select the arrangement for the electrodes 150(1)-150(N) and the stimulation mode of the current signals. In other embodiments, the controller 180 may be connectable to an external device (e.g., computer, remote control, etc.) via an interface. This can allow the user to select the arrangement for the electrodes 150(1)-150(N) and the stimulation mode of the current signals via the external device.

In certain embodiments, an electroporation control module, such as control module 175, may be fully integrated within an insertion tool presented herein. In other embodiments, only a portion of the electroporation control module 175 may be integrated within an insertion tool presented herein. For example, in one embodiment only the switching circuit 178 is integrated in the insertion tool and an interface for connection to an external device is provided for control over the switching circuit 178.

As noted above, prior to affecting electroporation of a recipient's nerve cells via an insertion tool, a treatment substance is first delivered into the cochlea so that the treatment substance is located in proximity to the nerve cells at the time the electroporation occurs. FIGS. 2 and 4 illustrate one example embodiment in which a substance delivery mechanism is integrated within the insertion tool 134.

More specifically, the substance delivery mechanism of insertion tool 134 is formed by a substance delivery lumen 152 and the syringe port 154. In operation, a syringe is fluidically coupled to the syringe port 154 and a treatment substance is forced from the syringe through the substance delivery lumen 152 and out from the distal end 128 into the cochlea 130. As shown in FIG. 4A, the substance delivery lumen 152 is integrated within the outer wall 188 of the insertion guide tube 136 defining a stimulating assembly insertion lumen 190.

It is to be appreciated that insertion tools in accordance with embodiments presented herein can comprise substance delivery mechanisms that are different from that shown in FIGS. 2 and 4. For example, in one alternative arrangement, the syringe port 154 can be replaced by a connection to another substance delivery device, such as a pump (e.g., an infusion pump), reservoir, etc. In an alternative arrangement, the substance delivery lumen can be located within the stimulating assembly insertion lumen, rather than integrated within the outer wall of the insertion guide tube.

FIGS. 6A and 6B illustrate a further arrangement that includes a collapsible substance delivery lumen located inside a stimulating assembly insertion lumen, rather than a lumen integrated within an outer wall of an insertion tool. More specifically, FIGS. 6A and 6B are cross-sectional views of a distal portion 629(A) of an insertion tool. As shown, the distal portion 629(A) comprises an outer wall 688(A) that defines a stimulating assembly insertion lumen 690(A). Located within the stimulating assembly insertion lumen 690(A) adjacent to the outer wall 688(A) is a collapsible substance delivery lumen 652. Although not shown in FIGS. 6A and 6B, a proximal end of the collapsible substance delivery lumen 652 is configured to be fluidically coupled to a substance delivery device, such as syringe, reservoir, pump, etc.

In certain arrangements, the distal portion 629(A) of the insertion tool cannot exceed the size of an opening in a recipient's cochlear through which the distal portion 629(A) is inserted. Due to these size constraints, the size of the stimulating assembly insertion lumen 690(A) is limited and, accordingly, substantially all of the stimulating assembly insertion lumen 690(A) may be needed to accommodate the stimulating assembly (i.e., the stimulating assembly may substantially fill the stimulating assembly insertion lumen 690(A)). These size constraints may limit the size of a substance delivery lumen, as well as where a substance delivery lumen may be located.

The collapsible substance delivery lumen 652 of FIGS. 6A and 6B provides a substantially large lumen for delivery of a treatment substance to a recipient while minimizing and/or eliminating a requirement for a larger distal portion 629(A) of an insertion tool. In particular, as shown in FIG. 6A, the collapsible substance delivery lumen 652 has a first expanded (non-compressed) configuration that enables a treatment substance to pass there through and exit out from a distal end 628(A) of the insertion tool. Although the expanded configuration of FIG. 6A allows for passage of the treatment substance, this expanded configuration also occupies a region of the stimulating assembly insertion lumen 690(A) that may be needed for insertion of the stimulating assembly. However, the collapsible substance delivery lumen 652 has a compressible arrangement such that, when a stimulating assembly is inserted into the stimulating assembly insertion lumen 690(A), the stimulating assembly will substantially collapse the delivery lumen 652 against the outer wall 688(A) (i.e., the collapsible substance delivery lumen 652 is compressed in response to pressure applied by a stimulating assembly introduced into the stimulating assembly insertion lumen 690(A)).

FIG. 6B illustrates the collapsible substance delivery lumen 652 in a collapsed (compressed) configuration. However, for ease of illustration, the stimulating assembly introduced into the stimulating assembly insertion lumen 690(A) to cause the compression of the collapsible substance delivery lumen 652 has been omitted from FIG. 6B.

FIG. 6C is cross-sectional view of another embodiment in which an insertion tool includes an alternative treatment substance delivery mechanism. More specifically, shown in FIG. 6C is an insertion guide tube 636 of an insertion tool. The insertion guide tube 636 includes an intra-cochlear section 645 and extra-cochlear section 647. The insertion guide tube 636 includes an outer wall 688(C) that defines a stimulating assembly insertion lumen 690(C).

An opening/inlet 691 is formed in the outer wall 688(C) at extra-cochlear section 647. Although not shown in FIG. 6C, this opening 691 is configured to be fluidically coupled to a substance delivery device, such as syringe, reservoir, pump, etc. so that a treatment substance may be delivered into the stimulating assembly insertion lumen 690(C). The delivery of a treatment substance to lumen 690(C) is generally represented in FIG. 6C by arrow 693.

As shown in FIG. 6C, when a treatment substance is delivered into the lumen 690(C), the stimulating assembly 118 is retracted so that the treatment substance is injected into an unobstructed section of the lumen with the distal end of the stimulating assembly positioned proximal to the injection site. In these embodiments, the stimulating assembly 118 can help propagate and mix the treatment substance within the cochlea as it is advanced through the stimulating assembly insertion lumen 690(C).

As noted, the above embodiments are illustrative of drug delivery mechanisms that may be incorporated within an insertion tool in accordance with embodiments presented herein. It is also to be appreciated that an insertion tool may be used with a treatment substance that is first delivered to a recipient's cochlea via a separate delivery device, such as a syringe, pump, etc. In such embodiments, the insertion tool is inserted into the cochlea after the treatment substance has already been delivered to the cochlea.

FIGS. 7A-7F are different views of embodiments of an insertion guide tube, referred to herein at insertion guide tube 736, forming part of an insertion tool in accordance with embodiments presented herein. The insertion guide 736 is representative of an embodiment for use with a pre-curved stimulating assembly. However, it is to be appreciated that these embodiments are merely illustrative and that the embodiments presented herein may be used with other devices configured for insertion of, for example, straight stimulating assemblies. For ease of description, features of the guide tube 736 will be described with reference to the orientation of the guide tube illustrated in the FIGS. 7A-7F.

Figure 7A:
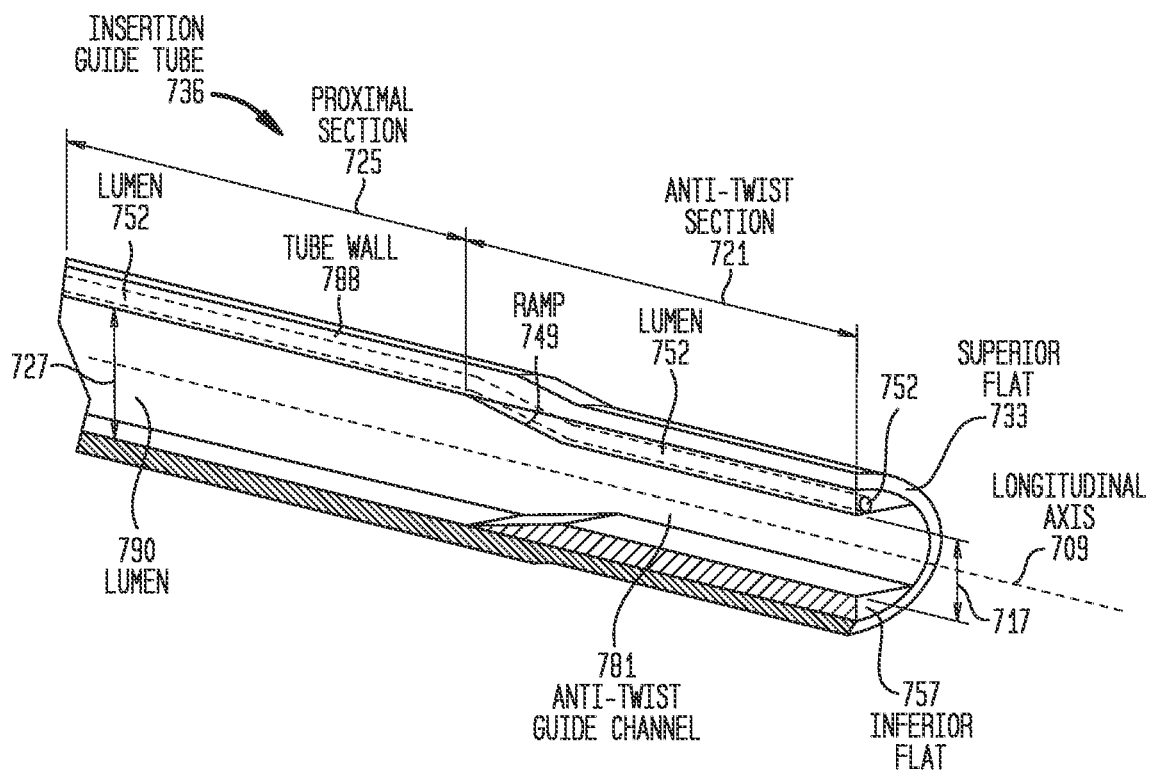
FIG. 7A is a cross-sectional view of an embodiment of an insertion guide tube in accordance with embodiments presented herein.
Figure 7B:
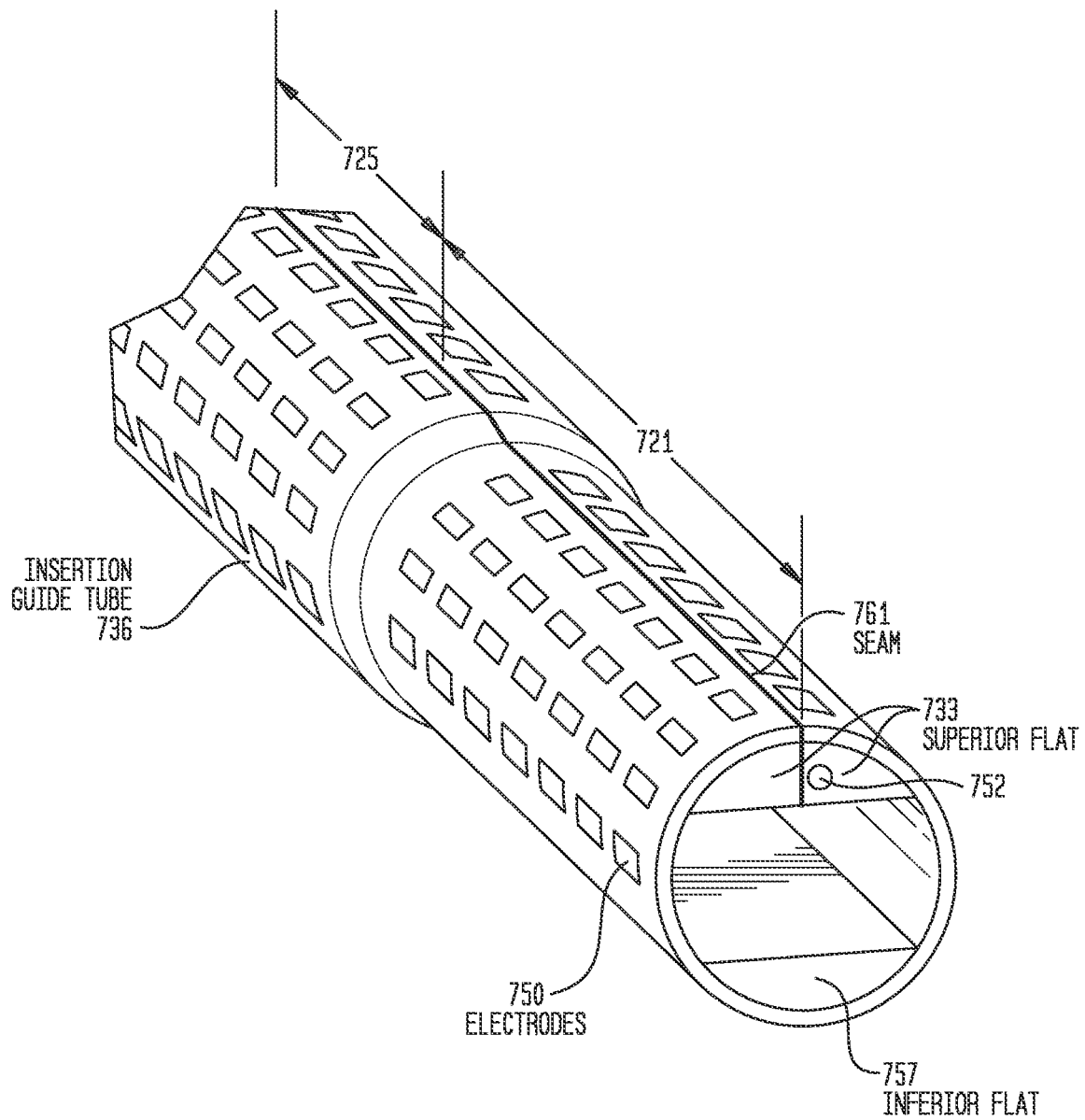
FIG. 7B is a perspective view of the portion of the insertion guide tube illustrated in FIG. 7A.

FIG. 7A is a partial cross-sectional view of an embodiment of insertion guide tube 736. As may be seen, insertion guide tube 736 includes an anti-twist section 721 formed at the distal end of the guide tube. Anti-twist section 721 is contiguous with the remaining part of guide tube 736. Guide tube 736 has an insertion lumen 790 which, in proximal section 725 has a vertical dimension 727 and in distal anti-twist section 721 has a smaller vertical dimension 717 described below. The vertical dimension of insertion lumen 790 decreases from dimension 727 to dimension 717 due to a ramp 749 at the proximal end of anti-twist section 721.

Anti-twist section 721 causes a twisted stimulating assembly traveling through guide tube 736 to return to its un-twisted state, and retains the stimulating assembly in a straight configuration such that the orientation of the stimulating assembly relative to the insertion guide tube 736 does not change.

Figure 7C:
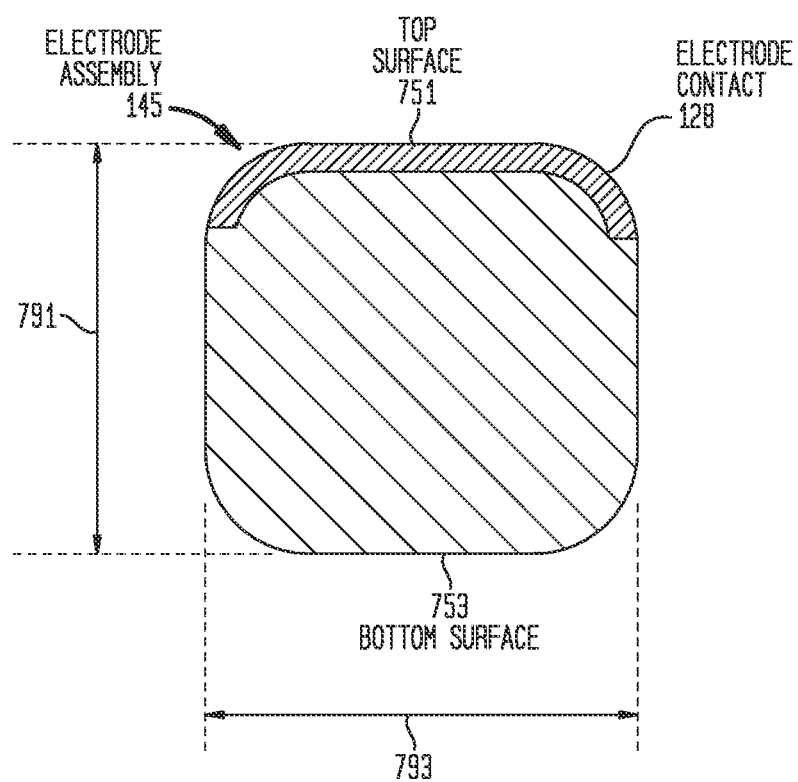
FIG. 7C is a cross-sectional view of a stimulating assembly for implantation into a recipient's cochlea.

As shown in FIG. 7C, stimulating assembly 118 has a rectangular cross-sectional shape, with the surface formed in part by the surface of the electrode contact, referred to herein as top surface 751, and the opposing surface, referred to herein as bottom surface 753, are substantially planar. These substantially planar surfaces are utilized in embodiments of the insertion guide tube described herein.

Tube wall 788 in anti-twist section 721 has surfaces 733 and 757 which extend radially inward to form an anti-twist guide channel 781. Specifically, a superior flat 733 provides a substantially planar lumen surface along the length of section 721. As shown best in FIGS. 7A, 7B and 7D, superior flat 733 has a surface that is substantially planar and which therefore conforms with the substantially planar top surface 751 of stimulating assembly 118. Similarly, inferior flat 757 has a surface that is substantially planar which conforms with the substantially planar bottom surface 753 of stimulating assembly 118. As shown in FIG. 7D, when a distal region of stimulating assembly 118 is located in anti-twist section 721, the surfaces of superior flat 733 and inferior flat 757 are in physical contact with top surface 751 and bottom surface 753, respectively, of the stimulating assembly.

Due to the longitudinal length of anti-twist guide channel 781, stimulating assembly 118 is unable to twist to relieve the stress caused by the inability of the stimulating assembly to assume its pre-curved configuration. This is illustrated in FIG. 7A. As shown by arrow 706 in FIGS. 7E and 7F, stimulating assembly 118 is attempting to twist while located in anti-twist section 721. As top surface 751 of stimulating assembly 118 pushes against superior flat 733, the flat applies a reactive force 704 to the assembly. Similarly, as bottom surface 753 of stimulating assembly 118 applies a force against inferior flat 757, that flat applies a reactive force 702 to the assembly.

Figure 7F:
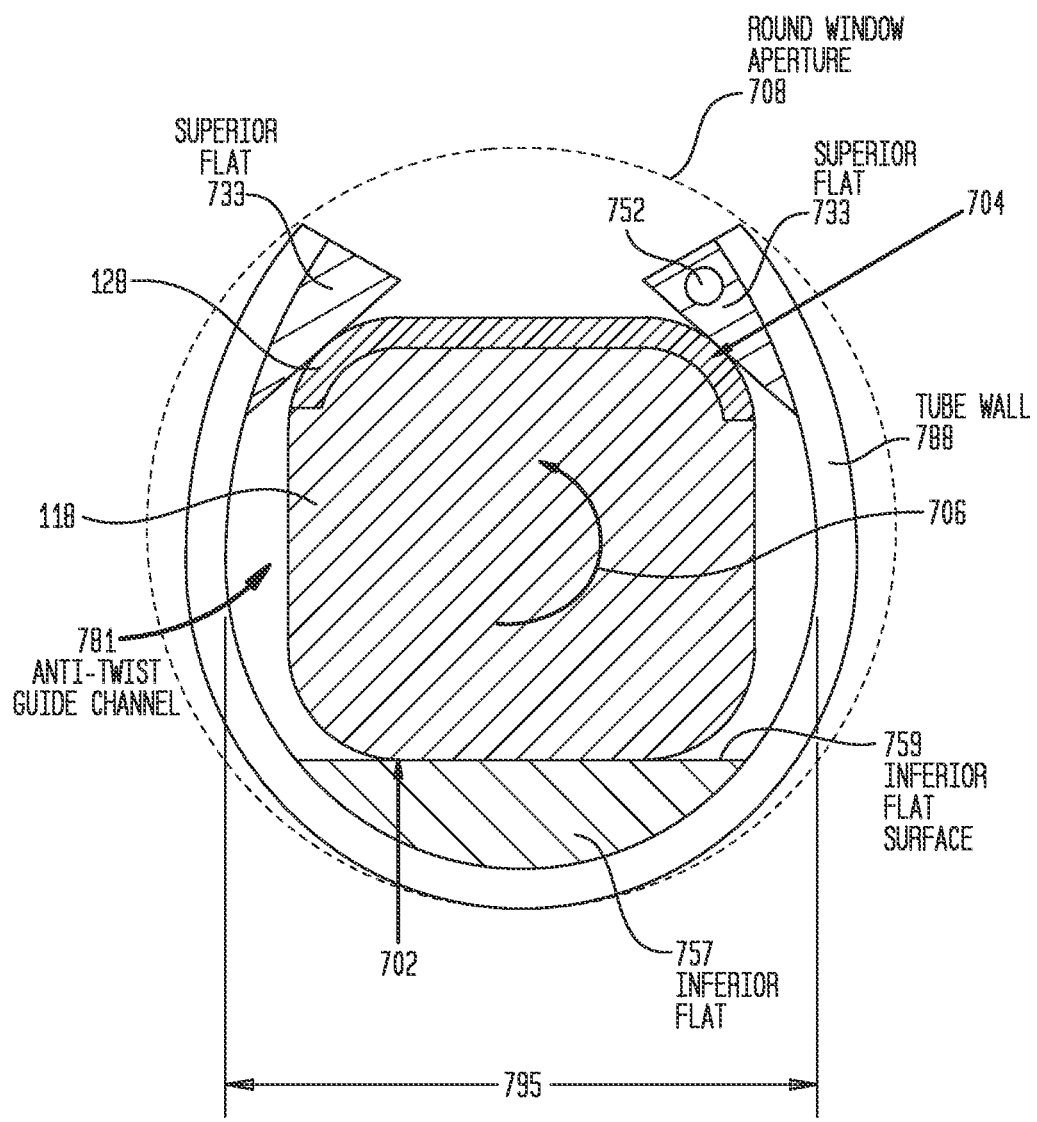
FIG. 7F is a cross-sectional view of the insertion guide tube splayed open to accommodate a larger-dimensioned proximal region of the stimulating assembly, with arrows representing the twisting force of the stimulating assembly and the reactive forces applied to the stimulating assembly by the insertion guide tube.

Stimulating assemblies may be longitudinally tapered. To accommodate the increasingly larger cross-sectional dimensions of a stimulating assembly 118 as it passes through anti-twist guide channel 781, insertion guide tube 736 has a longitudinal seam 761 as shown in FIGS. 7A, 7B, 7D, and 7E. This seam 761 enables insertion tube 736 to splay open as shown in FIG. 7F. Specifically, insertion tube 736 opens as the vertical distance 791 from bottom surface 753 to top surface 751 of the portion of the assembly in guide channel 781 becomes greater than the vertical distance 717 between the surfaces of inferior flat 757 and superior flat 733.

Once stimulating assembly 118 is inserted into cochlea 130, insertion guide tube 736 is retracted over stimulating assembly 118. The expanded insertion guide tube 736 is to be withdrawn from cochlea 130 and therefore is to pass through the cochleostomy, oval or round window. In a round window insertion, for example, splayed insertion guide tube 736 is to pass through round window aperture 708.

As stimulating assembly 118 is advanced through insertion guide tube 736, the tendency of the assembly to twist decreases. This is due to the increasingly greater portion of the stimulating assembly which has been deployed, the relatively larger dimensions of the proximal regions of the assembly, and the relatively smaller bias force in the proximal region as compared to the distal region of the assembly. Thus, as the cross-sectional size of the assembly passing through guide channel 781 increases, the tendency of the stimulating assembly to twist decreases. Referring again to FIG. 7F, as insertion guide tube 736 splays, the halves of bifurcated superior flat 733 each translate laterally to the corners of the stimulating assembly, and ultimately to opposing sides of the assembly. Thus, the extent to which superior flat 733 prevents the twisting of the stimulating assembly decreases with the tendency of the assembly to twist. And as noted, the outside diameter of insertion guide tube 736 does not exceed threshold value(s) which facilitate the withdrawal of the guide tube. In the example noted above with reference to FIGS. 7E and 7F, for example, insertion guide tube 736 has a diameter that is less than the round window aperture 708 when the guide tube is and is not splayed.

As shown in FIG. 7D, lumen 790 has a lateral dimension or width 795 which is greater than the analogous lateral dimension or width 793 of the distal region of stimulating assembly 118. This space is dimensioned to receive the wider stimulating assembly as the larger proximal region passes through guide channel 781.

In anti-twist section 721 there is a minimal gap, if any, between flats 733, 757 and stimulating assembly 118, thereby enabling anti-twist guide channel 781 to closely control the orientation of the assembly, as noted above. Should a region of stimulating assembly 118 located in proximal section 725 be partially twisted relative to a region that is in anti-twist guide channel 781, ramps 749 facilitate the rotation of the assembly as it enters the guide channel. This eliminates the relative twist of this region relative to a more distal region of the assembly. This places top and bottom surfaces 751, 753 in parallel with the corresponding surfaces of superior flat 733 and inferior flat 757 thereby enabling the assembly to continue through anti-twist guide channel 781. In other words, for the assembly to travel through guide channel 781, the assembly has to be substantially straight. As the assembly travels up ramp 749, the ramp facilitates the rotation of the assembly to enable the assembly to enter guide channel 781.

In an exemplary embodiment, insertion guide tube 736 is made of polyimide, and the flats comprise silicone molded in the tube. Other materials can be utilized in other embodiments. In some embodiments, the flats and guide tube are unitary.

FIGS. 7A-7F have been described above with reference to the operation of the insertion guide tube 736 during insertion of stimulating assembly 118 into a recipient's cochlea 130. As noted above, the insertion guide tube 736 is a component of a dual-function insertion tool. That is, in addition to enabling correct insertion of the stimulating assembly 118 into the cochlea 130, the insertion tool is further configured to deliver an electrical field to open pores in the cochlear nerve cells and thereby enable introduction of substances thereto. As such, the insertion guide tube 736 further comprises a plurality of electrodes 750 disposed on an outer surface of the tube wall 788. Similar to the above embodiments, the electrodes 750 are configured to generate an electrical field in the cochlea so as to affect electroporation of cochlear nerve cells. The plurality of electrodes 750 are electrically connected to a power supply by an electrical connection (not shown in FIGS. 7A-7F) extending through the insertion guide tube 736.

In addition to the plurality of electrodes 750, the insertion guide tube 736 also includes a substance delivery lumen 752 that delivers a treatment substance to the cochlea 130. In the example of FIGS. 7A-7F, within the proximal section 725 of the insertion guide 736, the substance delivery lumen 752 is integrated within the tube wall 788. The substance delivery lumen 752 is configured to follow the ramp 748 and is integrated within the superior flat 733 within the anti-twist section 721.

FIG. 8 is a method 800 for introducing a treatment substance into nerve cells of a cochlea with a surgical tool in accordance with embodiments presented herein. Method 800 begins at 802 where the surgical tool is positioned in the cochlea of a recipient (e.g., an intra-cochlear portion of the surgical tool is inserted into the cochlea). At 804, an electrical field is generated between at least two electrodes disposed on an intra-cochlea portion of the surgical tool. At 806, an electrode is advanced into the cochlea via the surgical tool. At 808, the surgical tool is withdrawn from the cochlea.

It is to be appreciated that the order of the operations shown in FIG. 8 is merely illustrative.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A surgical tool comprising:
a sheath configured to be inserted into a body chamber within the body of a recipient to guide a stimulating assembly of an implantable medical device into position within the body chamber,
wherein the sheath comprises a plurality of electrodes.

2. The surgical tool of claim 1, wherein the sheath forms a tube through which the stimulating assembly is advanced.

3. The surgical tool of claim 1, wherein the sheath comprises a thin-film circuit, and wherein the plurality of electrodes are formed on an outer surface of the thin-film circuit.

4. The surgical tool of claim 1, wherein the surgical tool has a proximal portion attached to the sheath that facilitates manipulation of the surgical tool during surgery.

5. The surgical tool of claim 1, wherein the body chamber comprises a cochlea of the recipient, and wherein the sheath is configured for insertion through a round window of the cochlea.

6. The surgical tool of claim 1, wherein the plurality of electrodes are formed into two or more functional groups of electrodes.

7. The surgical tool of claim 6, wherein the two or more functional groups of electrodes include a distal group of electrodes comprising electrodes located relatively closer to a distal end of the sheath, and a proximal group of electrodes comprising electrodes located relatively closer to a proximal end of the sheath.

8. The surgical tool of claim 1, wherein the surgical tool has at least one electrical connector configured to electrically connect the electrodes to a current source.

9. The surgical tool of claim 8, wherein the at least one electrical connector is configured to electrically connect the surgical tool to an external current source.

10. The surgical tool of claim 1, wherein the plurality of electrodes are electrically isolated from the implantable medical device.

11. The surgical tool of claim 1, wherein the surgical tool includes a substance delivery mechanism configured to deliver a treatment substance into the body chamber.

12. The surgical tool of claim 11, wherein the substance delivery mechanism comprises a substance delivery lumen configured to deliver the treatment substance into the body chamber.

13. The surgical tool of claim 12, wherein the substance delivery lumen is a collapsible lumen that is located inside the sheath.

14. An insertion tool for a stimulating assembly, comprising:
an insertion guide member configured to receive the stimulating assembly therein, wherein a distal portion of the insertion guide member is configured to be positioned within a body chamber of a recipient; and
one or more electrodes disposed on the distal portion of the insertion guide member, wherein the one or more electrodes are configured to apply an electrical field to the recipient.

15. The insertion tool of claim 14, further comprising:
a least one electrical connector configured to electrically connect the one or more electrodes to a current source; and
one or more leads extending from the one or more electrodes to the at least one electrical connector.

16. The insertion tool of claim 14, wherein the one or more electrodes comprise a plurality of electrodes formed into two or more functional groups of electrodes.

17. The insertion tool of claim 16, wherein the two or more functional groups of electrodes include a distal group of electrodes comprising electrodes located relatively closer to a distal end of the insertion guide member, and a proximal group of electrodes comprising electrodes located relatively closer to a proximal end of the insertion guide member.

18. The insertion tool of claim 14, wherein an outer surface of the insertion guide member comprises a thin-film circuit, and wherein the one or more electrodes are formed as part of the thin-film circuit.

19. The insertion tool of claim 14, further comprising:
a substance delivery mechanism configured to deliver a treatment substance into the body chamber.

20. The insertion tool of claim 19, wherein the substance delivery mechanism is a collapsible lumen that is located inside the insertion guide member.

21. The insertion tool of claim 19, wherein the treatment substance is at least one biological agent selected from the group including: Deoxyribonucleic acid (DNA), Ribonucleic acid (RNA) molecules, brain-derived neurotrophic factors, peptides, RNAi and viral vectors.

22. The insertion tool of claim 14, wherein the insertion guide member forms a tube through which the stimulating assembly is advanced.

23. The insertion tool of claim 22, wherein the insertion guide member includes a longitudinal seam that is configured to splay open as a force is applied to an interior surface of the insertion guide member via advancement of the stimulating assembly.

24. The insertion tool of claim 23, wherein the treatment substance is at least one biological agent selected from the group including: Deoxyribonucleic acid (DNA), Ribonucleic acid (RNA) molecules, brain-derived neurotrophic factors, peptides, RNAi and viral vectors.

* * * * *